(12) United States Patent
Cole et al.

(10) Patent No.: US 6,897,463 B1
(45) Date of Patent: May 24, 2005

(54) WAFER CARRIER MAPPING SENSOR ASSEMBLY

(75) Inventors: Samuel J. Cole, Portland, OR (US);
Ric DeHoff, Hillsboro, OR (US);
Edward D. Seeberger Jr., Portland, OR (US)

(73) Assignee: CyberOptics Semiconductor, Inc., Beaverton, OR (US)

( * ) Notice: Subject to any disclaimer, the term of this patent is extended or adjusted under 35 U.S.C. 154(b) by 338 days.

(21) Appl. No.: 10/190,744

(22) Filed: Jul. 8, 2002

Related U.S. Application Data
(60) Provisional application No. 60/305,176, filed on Jul. 13, 2001.

(51) Int. Cl.[7] .................................................. H01J 40/14
(52) U.S. Cl. ............................ 250/559.29; 250/559.33; 414/936
(58) Field of Search .................... 250/559.29, 559.33, 250/559.36, 559.4; 340/686.5; 356/614, 615; 414/936–938, 940, 941; 438/16

(56) References Cited

U.S. PATENT DOCUMENTS

| | | |
|---|---|---|
| 5,504,345 A | 4/1996 | Bartunek et al. ........ 250/559.4 |
| 6,188,323 B1 * | 2/2001 | Rosenquist et al. ...... 340/686.5 |
| 6,291,830 B1 | 9/2001 | Duquette ................. 250/559.3 |
| 2003/0141465 A1 * | 7/2003 | Schuda .................. 250/559.29 |

FOREIGN PATENT DOCUMENTS

FR  2664525 A1 * 1/1992 ............ B25J/15/06

OTHER PUBLICATIONS

U.S. Appl. No. 10/190,898, filed Jul. 8, 2002, Cole et al.

* cited by examiner

*Primary Examiner*—Stephone B. Allen
(74) *Attorney, Agent, or Firm*—Westman, Champlin & Kelly, P.A.

(57) ABSTRACT

A wafer mapping sensor assembly includes a housing, and an imaging array positioned therein. Imaging optics are positioned relative to the array to focus an image upon the array. An illumination source is configured to direct illumination toward the wafer, where such illumination is reflected by the wafer. An optical element is interposed between the source and the wafer. The optical element directs the illumination to reduce the effects of undesirable illumination.

18 Claims, 6 Drawing Sheets

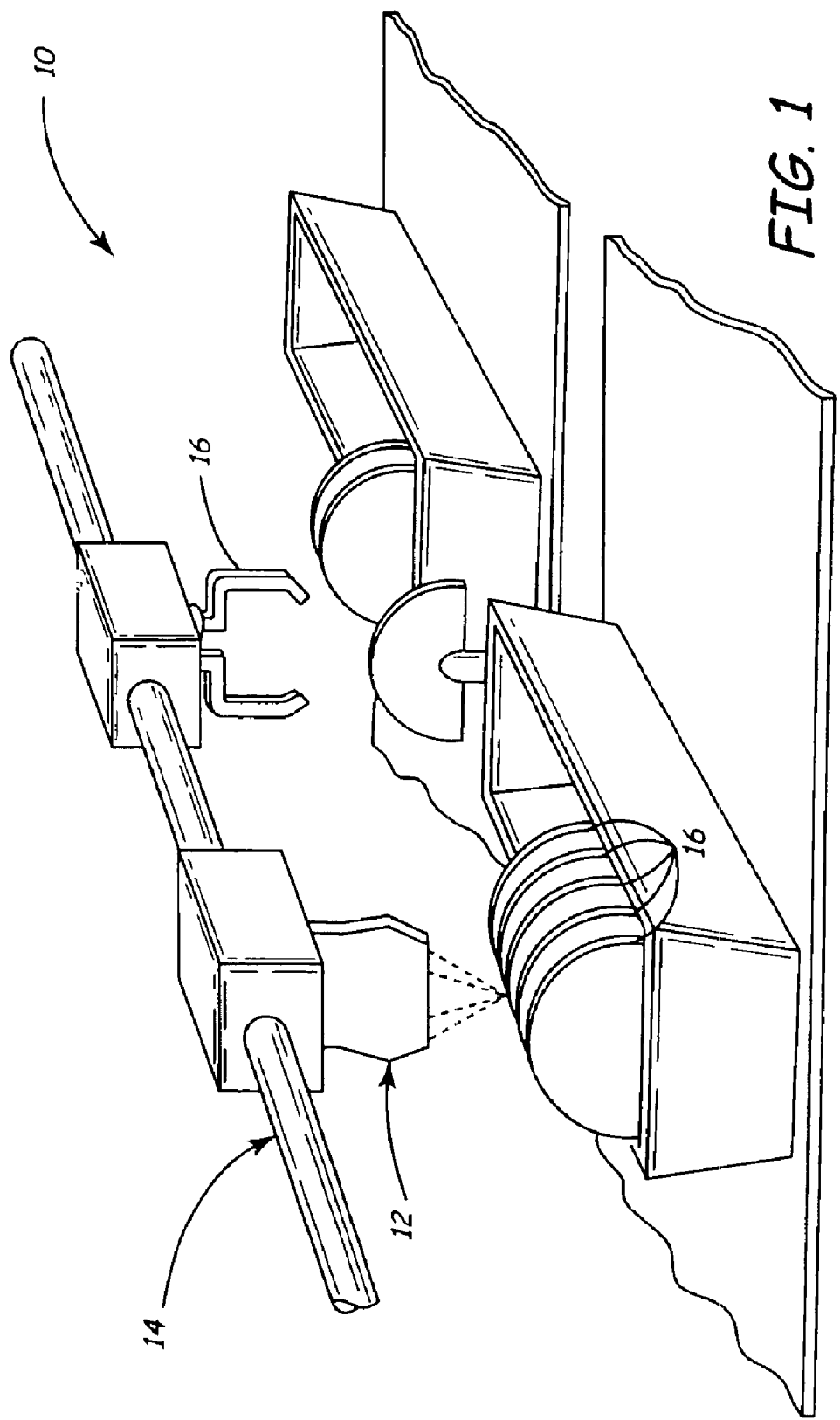

WAFER CARRIER MAPPING SENSOR ASSEMBLY

CROSS REFERENCE TO CO-PENDING APPLICATION

This application claims priority benefits from U.S. Provisional patent application Ser. No. 60/305,176, filed Jul. 13, 2001 and entitled "Wafer Mapping Sensor Assembly." This application is related to U.S. patent application Ser. No. 10/190,744, filed on even date herewith and entitled, "System for Mapping Wafers Using Predictive Dynamic Lighting."

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to wafer mapping systems.

BACKGROUND OF THE INVENTION

Wafer carrier mapping is an important element in semiconductor manufacturing. Each wafer may include many semiconductor chips and represent thousands of dollars worth of materials and time. Wafer carrier mapping is a process wherein errors can be detected and addressed before significant manufacturing losses occur. As used herein, "mapping wafers" means scanning a set of wafers in either a transport or storage cassette or pod, and determining which slots in the cassette or pod have wafers in them and whether any of the wafers are incorrectly placed. Preferably, a device in accordance with embodiments of the present invention is mounted on a wafer-handling robot (a known robotic system used in wafer manufacture), and maps the wafers as the robot arm moves in a generally vertical path in front of the cassette or pod.

Wafer carrier mapping systems use high-quality images to calculate location, thickness and correct slotting of one or more wafers in a carrier. One potential source of error present during the acquisition of such high-quality images is due to undesirable illumination being sensed by the imaging array. The only rays of illumination that are desirable during image acquisition are those that are reflected from a wafer surface. However, sometimes, a ray can be reflected from a non-wafer surface, such as a surface within a wafer cassette and generate erroneous image information. Thus, there is a need to provide a wafer carrier mapping sensor assembly that is less sensitive to the effects of undesirable illumination.

SUMMARY OF THE INVENTION

A wafer carrier mapping sensor assembly includes a housing, and an imaging array positioned therein. Imaging optics are positioned relative to the array to focus an image upon the array. An illumination source is configured to direct illumination toward the wafer, where such illumination is reflected by the wafer. An optical element is interposed between the source and the wafer. The optical element directs the illumination to reduce the effects of undesirable illumination.

BRIEF DESCRIPTION OF THE DRAWINGS

FIG. 1 is a diagrammatic view of a processing system in which embodiments of the present invention are particularly useful.

DETAILED DESCRIPTION

Figure 2A:
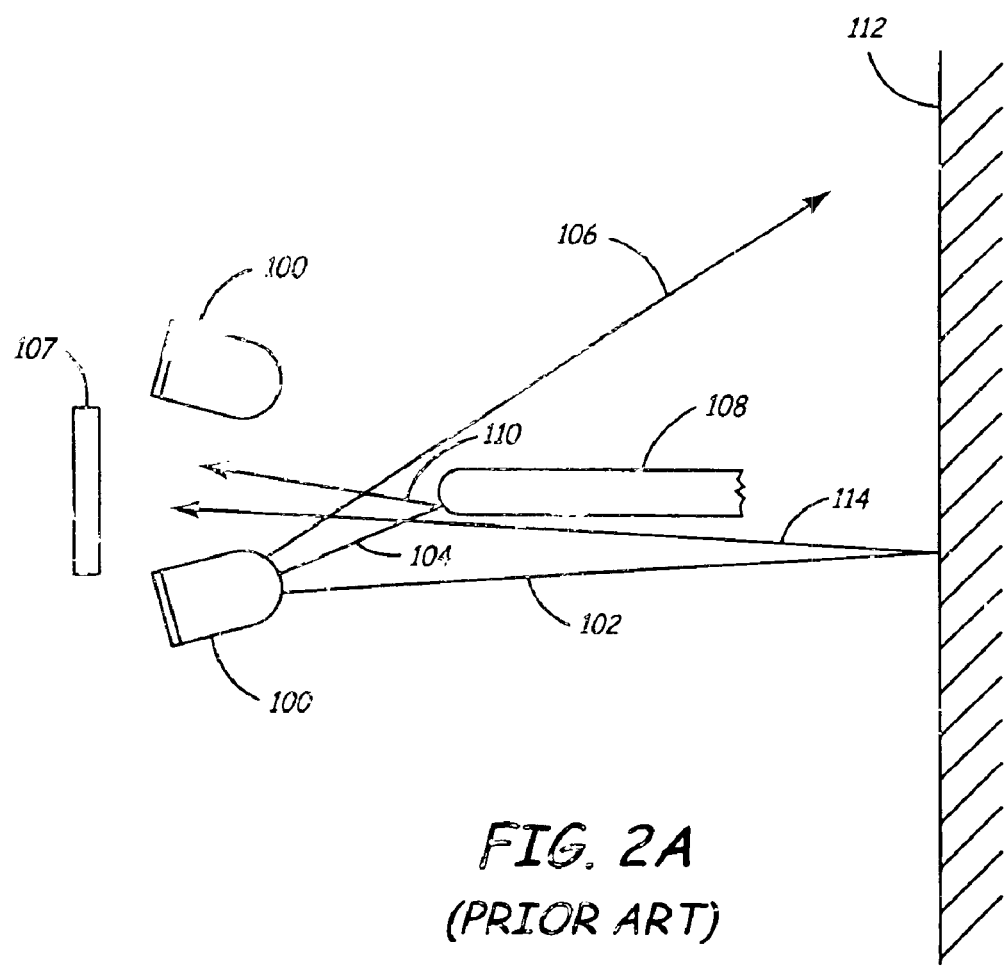
FIG. 2A is a diagrammatic view of a wafer mapping sensor in accordance with the prior art.

FIG. 1 is a diagrammatic view of a processing system in which embodiments of the present invention are particularly useful. Wafer processing system 10 includes a wafer carrier mapping system 12 coupled to robotic system 14, such that system 12 is movable relative to wafers 16. As system 12 moves past wafers 16, it provides an external signal indicative of wafer presence and/or wafer positioning errors. This signal is used by system 10 to direct the action of gripper 16 during wafer processing.

Embodiments of the present invention provide a wafer carrier mapping sensor assembly that uses a combination of optics and a placement of light sources, such as LEDs, to condition light for the purpose of imaging the edges of silicon wafers used in semiconductor manufacturing processes. Light produced by the LEDs is scattered off the edge of a wafer and then collected by an imaging system, which is preferably includes a charge coupled device (CCD). This light is imaged to produce a rendering of the wafer edge. The image is then processed to determine presence or absence of a wafer, along with a placement status measure of the wafer with respect to its manufacturing enclosure.

Embodiments of the present invention provide lighting features that balance two opposing design constraints. The first constraint is the need for high light intensity at the wafer edge so that very absorptive wafers can be imaged by the camera. The second constraint is the need to limit the amount of light that can be reflected off non-wafer surfaces which can cause erroneous results from the image processing.

Embodiments of the present invention provide a wafer carrier mapping sensor assembly that balances these two constraints through the use of an optical element that focuses the light at the wafer's edge, while at the same time deflecting the light such that the likelihood of extraneous reflections is diminished.

Figure 2B:
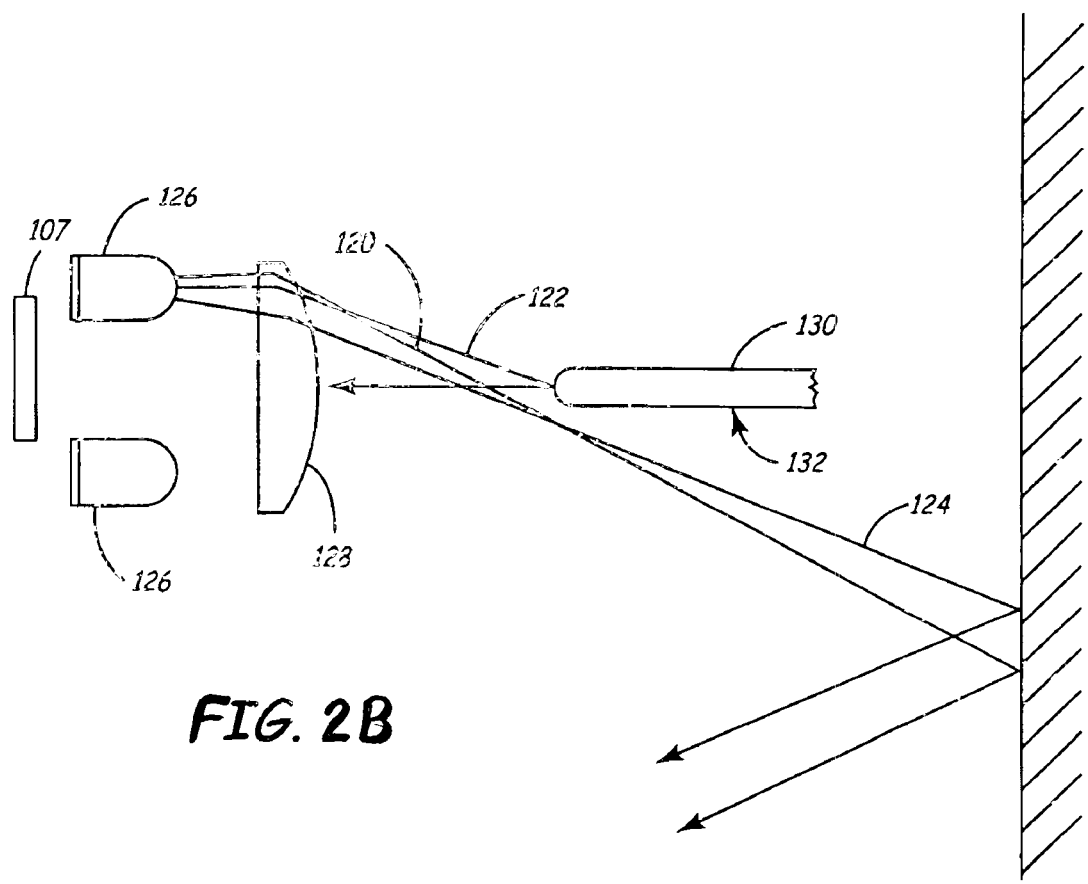
FIG. 2B is a diagrammatic view of a wafer mapping sensor in accordance with an embodiment of the present invention.

The manner in which these two ends are accomplished is illustrated in FIGS. 2A and 2B. In FIG. 2A, LEDs 100 provide illumination as illustrated by exemplary rays 102, 104 and 106. As can be seen, ray 106 is provided at such an angle that its reflected ray is not returned near LEDs 100. Ray 104, however, is reflected off an edge of wafer 108 and the reflected ray 110 passes between LEDs 100, which is typically where imaging array 107 is positioned. Ray 102, however, causes an undesired reflection. Specifically, ray 102 is reflected off surface 112, and the reflected ray 114 is provided near ray 110. Thus, contrast is reduced since undesired illumination, not reflected by the wafer, enters the array.

An embodiment of the present invention is illustrated in FIG. 2B. Rays 120, 122, and 124 from LEDs 126 are angled by passing through an off-axis portion of optics 128, which is preferably a cylindrical lens. This causes a large (approximately 5°) deflection of light rays 120, 122 and 124 relative to the plane 130 of the wafer to be imaged. Surfaces perpendicular and behind wafer 132 give the highest probability of reflections where the reflected light could be sent back to array 107. One example of such a surface is the back of a wafer carrier. A reflection off one of these surfaces can be picked up by the imaging system and cause a false readout from the sensor. By directing the light off axis to these back surfaces any light that is reflected does not have a path back to the imaging portion of the sensor assembly. Optics 128 also focuses the light in a single direction thus matching the long thin shape of the wafer edge. LEDs 126 themselves serve as small diffuse light sources whose profiles are preferably shaped to match the object to be illuminated.

Figure 3:
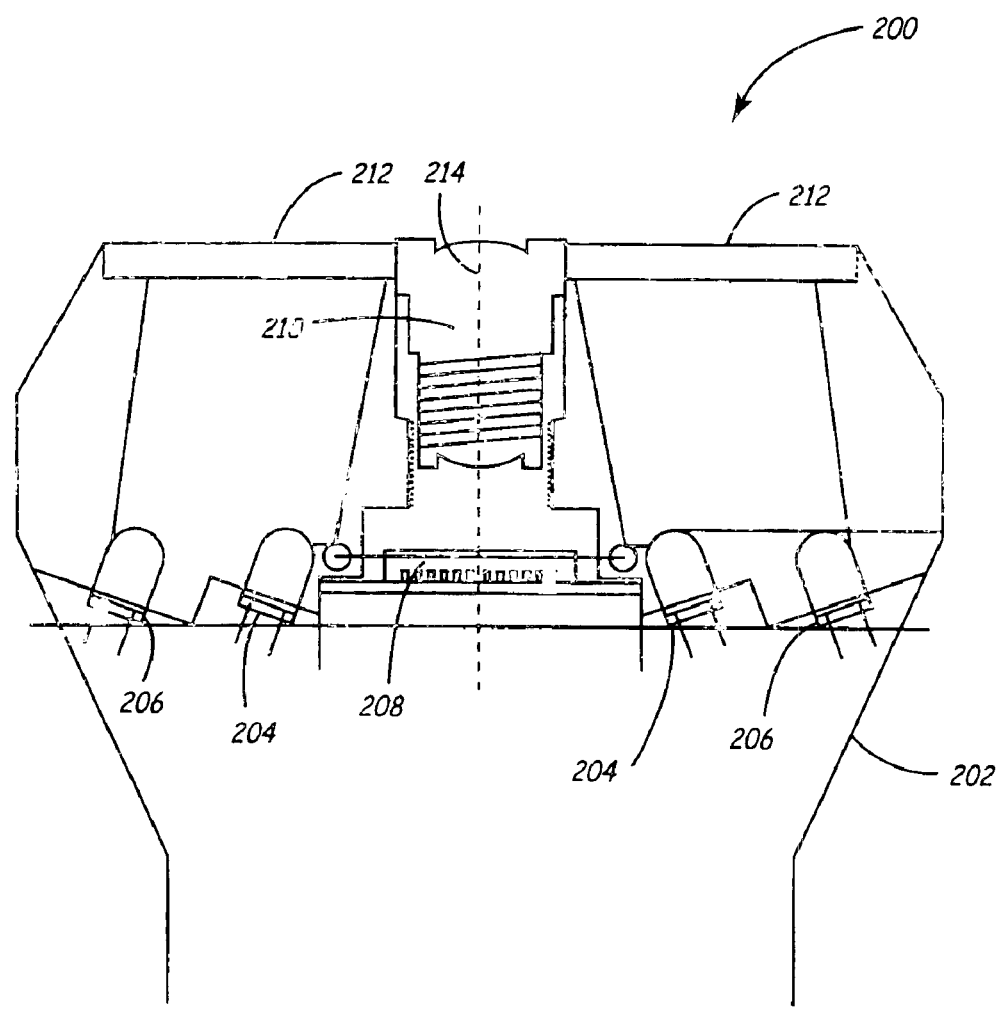
FIG. 3 is a diagrammatic view of a wafer mapping sensor assembly in accordance with an embodiment of the present invention.

FIG. 3 is a top plan view of wafer carrier mapping sensor assembly in accordance with an embodiment of the present invention. Sensor assembly 200 includes housing 202, light sources 204, 206, imaging array 208, lens 210, and optics 212. Sources 204, and 206 are preferably LEDs, and are mounted within housing 202 on opposite sides of array 208. Sources 204 are positioned relatively closely to array 208 and are preferably angled (at approximately 12 degrees) with respect to array axis 214. Sources 206 are positioned farther from array 208 and are also preferably angled (at approximately 18 degrees) with respect to array axis 214. Array 208 is preferably a Complementary Metal Oxide Semiconductor (CMOS) array that accumulates electrical charges in relation to the amount of light falling upon individual elements (pixels) during an exposure period. One example of array 208 is available from Eastman Kodak Company under the trade designation KAC-1011. Lens 210 is preferably a 6.1 mm diameter lens that is disposed to focus images upon array 208. However, array 208 can be any array of detectors, such as a Charge Coupled Device (CCD). Illumination from LEDs 204, 206 is bent by optics 212 as described above.

Figure 4A:
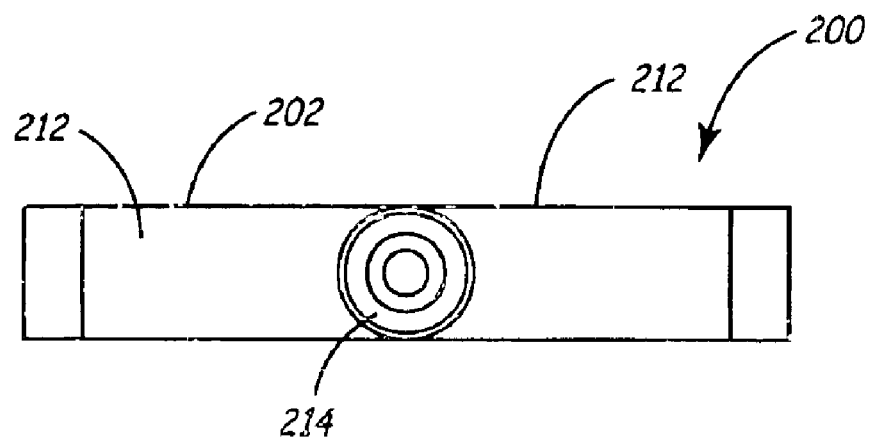
FIGS. 4A and 4B are front and side elevation views of a wafer mapping sensor assembly in accordance with the present invention.
Figure 4B:
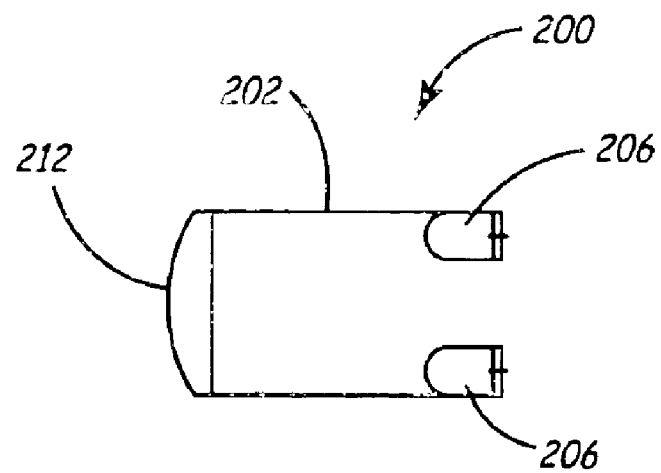

FIGS. 4A and 4B are front and side elevation views, respectively, of a sensor assembly 200 in accordance with an embodiment of the present invention. As can be seen in FIG. 4B, optics 212 is preferably a cylindrical lens having a curvature about an axis in the horizontal plane. Preferably, the radius of optics 212 is approximately 15.2 mm. The curvature was selected such that light would give a uniform illumination at the prescribed mapping distance of approximately 38.1 mm. Alternatively, distinct lenses could be positioned in front of other light sources to provide such uniform illumination. FIG. 4B also shows a pair of sources 206 spaced vertically with respect to one another. Thus, in the preferred embodiment, a total of four (4) LEDs are used for sources 204 and four (4) more are used for sources 206.

Figure 5:
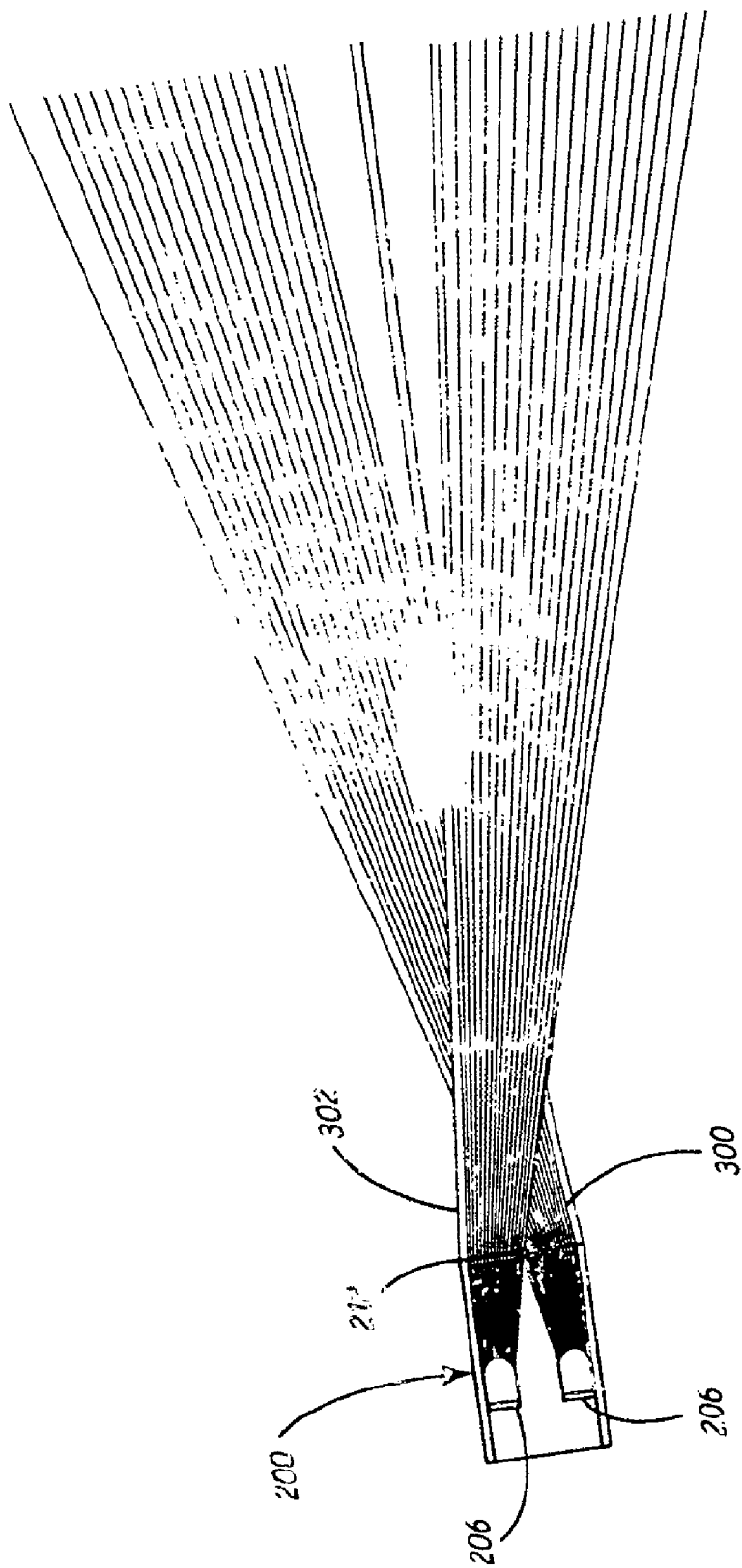
FIG. 5 is a ray diagram illustrating operation of a wafer mapping sensor assembly in accordance with an embodiment of the present invention.

FIG. 5 is a diagrammatic view of rays emanating from wafer carrier mapping sensor assembly 200. Rays begin at sources 206 and pass through lens 212. Bottom rays 300 are bent upwardly and top rays 302 are bent downward. As described above, the focal length of optics 212 is selected to direct at least some of the bottom rays 300 and top rays 302 upon an edge of wafer 132. Rays that do not impinge upon the wafer edge are thus provided in a direction that ensures that such rays will not be reflected and return to the camera.

The nominal off-axis angle produced by optics 212 is approximately 5 degrees, but can be varied without departing from the spirit and scope of the invention.

Normally, using the off-axis portion of a singlet lens such as this would produce unacceptable geometric distortions in the refracted light. Certainly this would be true if the light were to be used directly for imaging. In this case, however, the light wave distortion is of little consequence since only reflection and scatter of the wafer edge is collected by the array and lens.

The task of illuminating a silicon wafer edge for imaging purposes while lowering the chance of reflection could be accomplished with alternate techniques, however such techniques generally suffer from a number of disadvantages. A first alternate technique includes illuminating the wafer from the side. Typically the scanning of the wafer is accomplished by a robot moving in front of a cassette of wafers. If the side of the cassette contained bright light sources pointed perpendicular to the imager, the image could be created with very little chance of reflections disrupting the results. For the wafer mapper embodiment discussed herein, however, one design constraint was to have the entire sensor fit inside a housing shaped like that of a known wafer carrier mapping sensor. By so designing a sensor assembly, the necessity of pod/cassette modifications is removed thus facilitating widespread incorporation of the wafer carrier mapping sensor assembly in wafer carrier mapping systems. This design constraint meant that both the imager and the illumination source had to reside in a relatively small volume (approximately 0.5"×2.5"×3"). The size constraint did not allow the light sources to be angled at angles even approaching perpendicular to the imaging lens.

A second alternate technique involves the use of directed laser sources to accomplish the same task. Theoretically an array of lasers could replace the LED/cylindrical lens combination by angling the lasers at off axis angles relative to the wafer's level line. The drawback of this approach is mainly cost. A relatively large number of lasers sources would need to be used in order to create a reliable image of the wafer edge. Because the wafer edge profile is round, a laser source is imaged very close to a point source. Only a small point of the wafer's edge is imaged by a laser. In order to reliably determine presence and absence of a wafer and the error state of the object, twelve (12) or more lasers would likely be needed. The lasers would most likely still benefit from some kind of optics in front of them, so the cost of a laser-based design could multiply the cost of the entire optical package by a factor of 10 or more. The use of LEDs in sensor assembly 200 also provided the benefit of being a diffuse, albeit small, light source, which could be somewhat directed by geometric placement.

Although the present invention has been described with reference to preferred embodiments, workers skilled in the art will recognize that changes may be made in form and detail without departing from the spirit and scope of the invention. For example, although the illumination sources described above are generally LEDs, they are simply one example of suitably bright illumination sources. However, other suitably bright illumination sources could also be used, and such applications are expressly contemplated.

What is claimed is:

1. A wafer carrier mapping sensor assembly for detecting at least one wafer in a carrier, the at least one wafer having a wafer plane, the assembly comprising:

a housing;

a two-dimensional imaging array disposed within the housing;

imaging optics disposed relative to the array to focus an image upon the array; and at least one light source disposed to only direct light toward the wafer at a non-zero angle with respect to the array plane of the wafer.

2. The assembly of claim 1, and further comprising an optical element disposed relative to the at least one light source to pass off-axis bend light therethrough.

3. The assembly of claim 2, wherein the optical element is a cylindrical lens.

4. The assembly of claim 1, wherein the at least one illumination source is disposed within the housing.

5. The assembly of claim 1, wherein the at least one illumination source comprises a light emitting diode.

6. The assembly of claim 5, wherein the illumination source comprises at least two pairs of light emitting diodes, each pair including a light emitting diode disposed within the case on opposite sides of the imaging array.

7. The assembly of claim 6, wherein at least one pair of light emitting diodes is disposed farther from the imaging array than another pair.

8. The assembly of claim 5, wherein the light emitting diodes are disposed at an angle based upon their distance from the imaging array.

9. The assembly of claim 1, wherein the at least one illumination source includes eight (8) light emitting diodes.

10. The assembly of claim 1, wherein the at least one light source includes a laser light source.

11. The assembly of claim 10, wherein the at least one light source includes twelve laser light sources.

12. The assembly of claim 1, wherein the imaging array is a CCD array.

13. The assembly of claim 1, wherein the imaging array is a CMOS array.

14. A method of mapping at least one wafers having a wafer plane in a wafer carrier, the method comprising:

providing a two-dimensional imaging array;

directing light solely at non-zero angles relative to the wafer plane;

imaging light reflected from the at least one wafer;

and generating an output based on the imaged reflected light.

15. The method of claim 14, wherein directing the light at non-zero angles relative to the wafer array includes passing the light through an optical element off-axis.

16. The method of claim 15, wherein the optical element is a cylindrical lens.

17. The method of claim 14, wherein the non-zero angles have an absolute value in excess of approximately 5 degrees.

18. A wafer carrier mapping assembly for detecting at least one wafer in a carrier, the at least one wafer having a wafer plane with first and second sides, the assembly comprising:

a housing;

a two-dimensional imaging array disposed within the housing;

imaging optics disposed relative to the array to focus an image upon the array; and at least one light source disposed to generate light on a first side of the wafer plane, and direct the light such that light either impinges the wafer, or passes on the second side of the wafer plane.

* * * * *

UNITED STATES PATENT AND TRADEMARK OFFICE
CERTIFICATE OF CORRECTION

PATENT NO.   : 6,897,463 B1                                         Page 1 of 1
DATED        : May 24, 2005
INVENTOR(S)  : Samuel J. Cole et al.

It is certified that error appears in the above-identified patent and that said Letters Patent is hereby corrected as shown below:

Column 5,
Line 5, delete "array".
Line 8, delete "bend".

Column 6,
Line 1, "wafers" should be -- wafer --.

Signed and Sealed this

Twenty-third Day of August, 2005

JON W. DUDAS
*Director of the United States Patent and Trademark Office*